United States Patent
Iida (10) Patent No.: US 10,398,584 B2
(45) Date of Patent: Sep. 3, 2019

(54) ANKLE SUPPORTER

(71) Applicant: OPTI LTD., Hiroshima (JP)

(72) Inventor: Takuji Iida, Nara (JP)

(73) Assignee: OPTI LTD, Hiroshima (JP)

( * ) Notice: Subject to any disclaimer, the term of this patent is extended or adjusted under 35 U.S.C. 154(b) by 438 days.

(21) Appl. No.: 14/913,070

(22) PCT Filed: May 29, 2014

(86) PCT No.: PCT/JP2014/064327
§ 371 (c)(1),
(2) Date: Feb. 19, 2016

(87) PCT Pub. No.: WO2015/181932
PCT Pub. Date: Dec. 3, 2015

(65) Prior Publication Data
US 2016/0206462 A1 Jul. 21, 2016

(51) Int. Cl.
*A61F 5/00* (2006.01)
*A61F 5/01* (2006.01)
*A61F 13/06* (2006.01)
*A41B 11/00* (2006.01)

(52) U.S. Cl.
CPC .......... *A61F 5/0111* (2013.01); *A61F 13/066* (2013.01); *A41B 11/003* (2013.01); *A41B 11/004* (2013.01); *A41B 2400/32* (2013.01)

(58) Field of Classification Search
CPC .... A61F 5/0111; A61F 5/0113; A61F 13/066; A61F 13/064; A61F 13/06; A61F 5/0585; A61F 5/05841; A61F 5/0104; A61F 5/01; A61F 13/065; A61F 13/067; A41B 11/003; A41B 11/004; A41B 2400/32; A43B 7/20; A43B 7/18; A43B 7/14
See application file for complete search history.

(56) References Cited

U.S. PATENT DOCUMENTS

| | | | | |
|---|---|---|---|---|
| 4,523,394 A | * | 6/1985 | Lindh | A61F 5/0111 36/114 |
| 6,286,151 B1 | * | 9/2001 | Lambertz | A41B 11/003 2/239 |
| 2007/0049857 A1 | * | 3/2007 | Quinn | A61F 5/0111 602/27 |

FOREIGN PATENT DOCUMENTS

| | | |
|---|---|---|
| JP | 2007332470 A | 12/2007 |
| JP | 2009050418 A | 3/2009 |
| JP | 2009155763 A | 7/2009 |
| JP | 2009524744 A | 7/2009 |
| JP | 4447559 B2 | 4/2010 |
| JP | 4602953 B2 | 12/2010 |

(Continued)

*Primary Examiner* — Victoria J Hicks
(74) *Attorney, Agent, or Firm* — Bacon & Thomas, PLLC (57) ABSTRACT

Provided is an ankle supporter capable of returning the wearer's ankle to a normal position by moving the connective tissue and muscles below the skin following sprain or Achilles tendonitis. The ankle supporter includes a first elastic panel knitted in a belt-like shape on the medial side of the wearer's foot extending from the sole to an area corresponding to the Achilles tendon and having a stretch resistance greater than that of the base fabric and a second elastic panel knitted in a belt-like shape on the medial side of the wearer's foot extending from the heel to the base of the foot top of the wearer to intersect the first elastic panel below the center of the medial ankle and having a stretch resistance greater than that of the base fabric.

4 Claims, 8 Drawing Sheets

(56) References Cited

FOREIGN PATENT DOCUMENTS

WO 2011090191 A1 7/2011
WO 2011090193 A1 7/2011

* cited by examiner

ANKLE SUPPORTER

TECHNICAL FIELD

The present invention relates to an ankle supporter.

BACKGROUND

The ankle joint includes the talocrural and subtalar joints, which connect the calcaneus with the talus and the talus with the lower leg bones composed of the tibia and fibula, respectively. Ankle sprain is an injury that frequently occurs in sports. Following injury, the medial aspect of the talus often exhibits reduced posterior gliding during ankle dorsiflexion (extension). The lateral ligaments are often stretched or torn, and osteocartilage injury can occur. Therefore, there has been a demand to develop a supporter or a brace that can effectively prevent ankle sprain.

A pair of socks of the prior art may be obtained by setting a first structure that can apply tension in the wale direction extending from a position behind the ball of the foot at the sole of the socks to a position that includes the boundary between the arch and the heel, setting a second structure that can apply increased tension along the periphery of the rear side of the ball, setting a third structure that can apply increased tension along the periphery of the ankle, and setting a fourth structure that can apply increased tension extending along the periphery from a position that includes the boundary between the arch and the heel to an area at the top of the foot (for example, see Patent Document 1).

CITATION LIST

Patent Document

Patent Document 1: JP 2009-155763 A

SUMMARY OF THE INVENTION

Problem to be Solved by the Invention

In socks of prior art, the longitudinal and transverse arches are supported and/or restored by elastic belts, and the positions of the elastic belts remain stable when the person wears the socks. However, those socks were not designed to improve ankle stability or correct ankle joint alignment, and therefore do not modify or improve adhesions of the subcutaneous connective tissues and/or muscles following sprain or Achilles tendonitis.

The present invention has been developed to solve the problems described above. The objective is to provide an ankle supporter capable of improving ankle alignment and motion by mobilizing adhesions of the subcutaneous connective tissues and muscles following sprain or Achilles tendonitis.

Means for Solving the Problem

The ankle supporter according to the invention includes the first elastic belt-like panel with greater stretch resistance than the base fabric on the medial side of the wearer's foot extending from just posterior to the ball of the foot over the navicular tuberosity and medial malleolus to the muscle tendon junction of the Achilles tendon. Therefore, the soleus of the wearer has an angle of 45 degrees relative to the sole of the foot. The second belt-like panel with greater stretch resistance than the base fabric is positioned on the medial side of the wearer's foot extending from the heel over the medial malleolus to the front of the ankle joint of the wearer. Then, the center of these two belts intersects about 1-4 cm below the top of the medial malleolus.

Effect of the Invention

The ankle supporter according to the invention can help the medial talus glide posteriorly during dorsiflexion of the ankle joint relative to the shank bones composed of the tibia and fibula. This is accomplished by applying tension on the first belt-like panel connecting the ball of the foot and medial malleolus. Accordingly, since the ankle joint regains normal dorsiflexion motion and has improved conformity of the talocrural joint, the ankle joint gains improved stability and thus reduces the risk of ankle sprain.

BRIEF DESCRIPTION OF DRAWINGS

FIG. 2(a) illustrates the ankle supporter according to the first embodiment as it would be worn on the right foot, while

8(b) is a lateral view of the ankle supporter shown in FIG. 7(a).

MODE(S) FOR CARRYING OUT THE INVENTION (First Embodiment of the Invention)

A right ankle supporter 100 will be described below with reference to FIG. 1. However, since the left ankle supporter 100 differs from the right ankle supporter 100 only in that the first elastic panel 1, second elastic panel 2, third elastic panel 3, fourth elastic panel 4, and fifth elastic panel 5 of the left ankle supporter are bilaterally symmetrical to those of the right ankle supporter, the left ankle supporter will not be shown in the drawings.

Further, in FIG. 1, a supporter with an open toe is shown as the ankle supporter 100, but a sock-type supporter with a closed toe bag may be used.

Figure 2A:
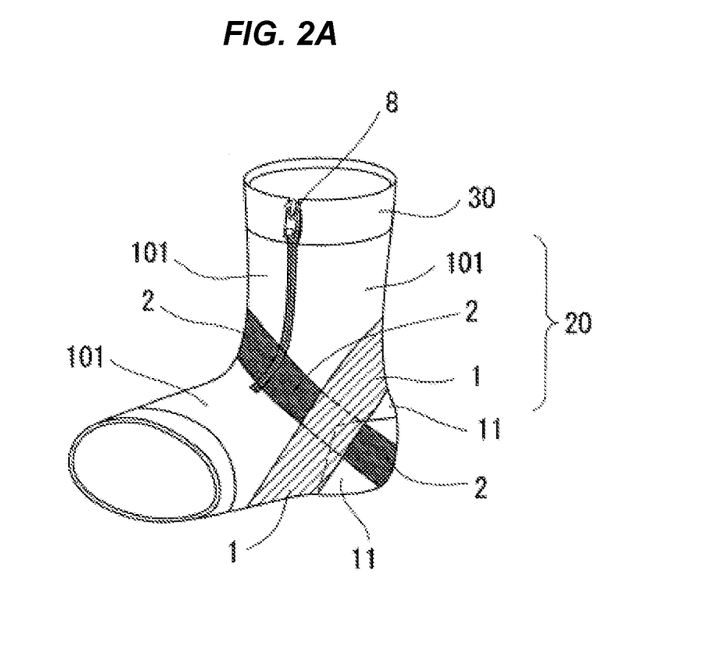
Figure 2B:
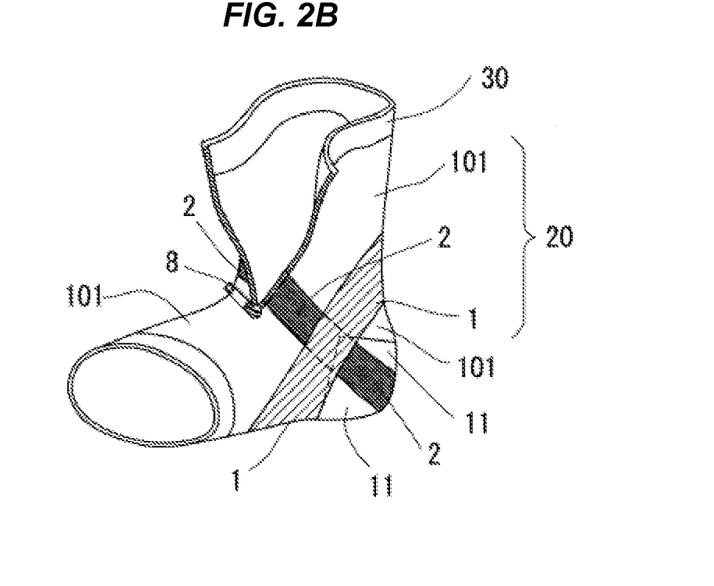
FIG. 2(b) shows the same ankle supporter as shown in FIG. 2(a) but with the zipper open.

Further, the ankle supporter 100 may include a zipper 8 (a fastener) used to open and close the body 20 at the top as shown in FIG. 2, and a hook-and-loop fastener, lacing, or a magic belt (trademark) may be used instead of the zipper 8.

Figure 1A:
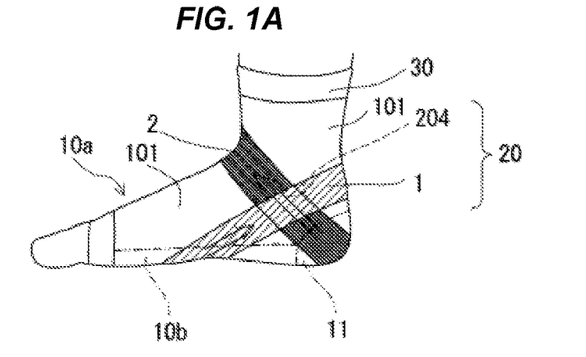
FIG. 1(a) is an explanatory diagram illustrating the effect obtained by the first and second panels located at ideal positions.

According to the embodiment shown in FIG. 1(a), the ankle supporter 100 surrounds at least the wearer's ankle with a base fabric 101 and includes a first elastic panel 1 which is disposed in a belt-like shape on a first part of the base fabric 101 corresponding to the medial surface of the wearer's foot extending from the sole to the area corresponding to the wearer's Achilles tendon. This first panel 1 has a stretch resistance greater than that of the base fabric 101. A second elastic panel 2 is disposed in a belt-like shape on a second part of the base fabric 101 corresponding to the medial surface of the wearer's foot extending from the heel to the base of the top so as to intersect the first elastic panel 1 at an area corresponding to the center of the wearer's medial ankle while remaining below the first elastic panel. This second panel 2 also has a stretch resistance greater than that of the base fabric 101.

Figure 1B:
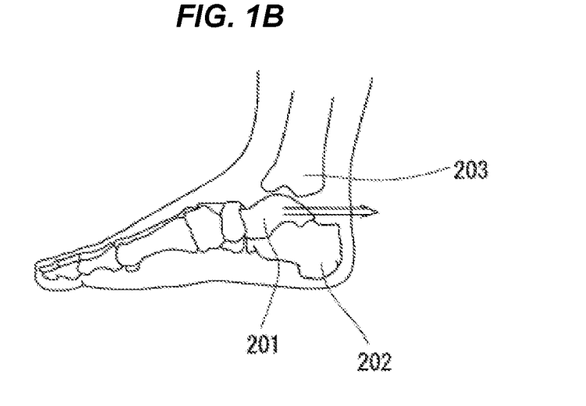
FIG. 1(b) is an explanatory diagram illustrating the effect of the first and second panels on the motion of the talus.
Figure 1C:
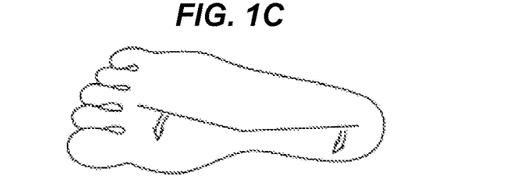
FIG. 1(c) is an explanatory diagram illustrating the effect obtained by the first and second panels on foot alignment reducing the angle between the rear and front of the foot.
Figure 1D:
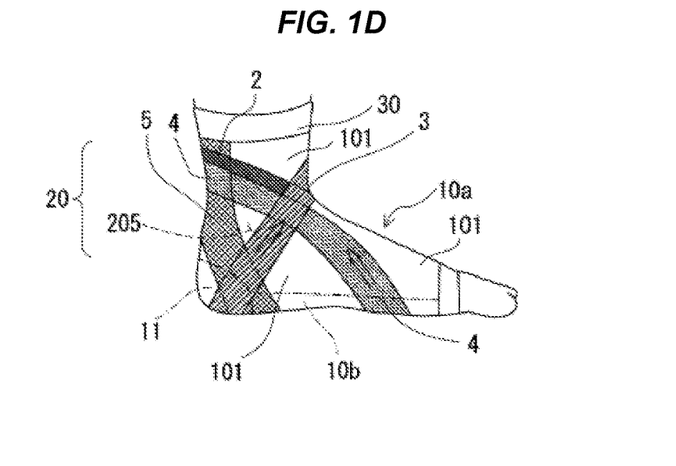
FIG. 1(d) is an explanatory diagram illustrating the effect obtained by a third elastic panel, a fourth elastic panel, and a fifth elastic panel located at ideal positions.

Further, according to the embodiment shown in FIG. 1(d), the ankle supporter 100 includes a third elastic belt-like panel 3 which is disposed on a third part of the base fabric 101 corresponding to the lateral side of the wearer's foot from the heel extending over the ankle to the medial side of the wearer's foot. This third elastic panel 3 has a stretch resistance greater than that of the base fabric 101. A fourth elastic belt-like panel 4 is disposed on a fourth part of the base fabric 101 corresponding to the lateral side of the wearer's foot extending from the area of the sole near the fifth toe of the wearer along the lateral portion of the foot so as to connect to the third elastic panel 3 in the area of the lateral ankle. This fourth elastic panel 4 also has a stretch resistance greater than that of the base fabric 101. A fifth elastic belt-like panel 5 is disposed on a fifth part of the base fabric corresponding to the lateral side of the wearer's foot extending from the heel along the back of the foot and connecting to the band 30 encircling the lower leg above the ankle. This fifth elastic panel 5 also has a stretch resistance greater than that of the base fabric 101.

Further according to the embodiment, the stretch resistance of the sole 10b is greater than that of the base fabric 101.

As shown in FIG. 1(b), the first elastic panel 1 can restore the talus 201 to an appropriate position between the calcaneus 202 and the tibia 203 by applying tension to the anterior talus 201 so that the tarsus glides in the posterior direction between the calcaneus 202 and the tibia 203 during dorsiflexion of the foot. Accordingly, the ankle can regain normal movement.

Additionally, the calcaneus 202 below the talus 201 moves toward the lateral heel in response to movement of the talus 201 due to tension applied by the first elastic panel 1. Accordingly, the lateral longitudinal arch of the foot is decreased and the burden is placed on the medial longitudinal arch.

For this reason, the second elastic panel 2 pulls the lateral heel in the medial direction as shown in FIG. 1(a) so as to prevent the calcaneus 202 from moving toward the lateral heel in response to the movement of the talus 201 due to tension applied by the first elastic panel 1. Accordingly, the medial longitudinal arch can be protected.

During daily life, dorsiflexion of the foot is frequently performed. For example, dorsiflexion of the foot occurs in the squatting position. Particularly, the squatting position places a great burden on the ankle since the body weight is loaded onto the ankle in that position.

However, the first elastic panel 1 and the second elastic panel 2 can promote smooth movement of the knees forward by establishing a stable positional relationship among the talus 201, calcaneus 202, and tibia 203 during movement into the squatting position. Accordingly, the burden on the ankle can be reduced.

In particular, during dorsiflexion of the foot, the second elastic panel 2 is contracted while the first elastic panel 1 is stretched. Therefore, the first elastic panel 1 has the effect of raising the arch of the wearer's foot by applying tension to the sole 10b.

FIG. 1(c) shows that as tension is applied, a wearer with a flat foot would experience longitudinal pressure that would direct the toes laterally. For this reason, in order to solve the problem of the flat foot, it is necessary to direct the toes medially following the longitudinal direction of the foot.

Since according to the embodiment, the ankle supporter 100 is composed of a knitted fabric in which the sole 10b minimally extends, lateral movement of the toes can be suppressed. Further, since the second elastic panel 2 pulls the lateral heel medially, the problem of the flat foot can be improved.

That is, according to the embodiment, the sole 10b supports the arch of the foot so that the wearer assumes a normal posture and the talus 201 glides between the calcaneus 202 and the tibia 203.

Further, according to the embodiment shown in FIG. 1(d), the ankle supporter 100 can suppress necrosis of the inside of the wearer's foot since the third elastic panel 3 and the fourth elastic panel 4 pull the lateral foot upward (the lateral foot hardly extends compared to the medial foot) and the downward movement of the fifth toe during plantar flexion (bending) of the foot can be suppressed since the fourth elastic panel 4 pulls the fifth toe obliquely upward (the fifth toe extends much less than the first toe).

That is, according to the embodiment of the ankle supporter 100, when the wearer is walking on a surface with a lateral downward slope, the third elastic panel 3 and the fourth elastic panel 4 cause the wearer to place weight on the medial toes while the fourth elastic panel 4 elevates the lateral toes. Accordingly, it is possible to prevent the lateral toes from touching the downward slope earlier than the medial toes and hence prevent sprain or stumbling due to over supination.

In particular, according to the embodiment of the ankle supporter 100, the medial and lateral regions are pulled toward each other. Accordingly, the wearer's ankle can be further stabilized and the tension can be maintained due to the first elastic panel 1 and the second elastic panel 2 on the medial side and the third elastic panel 3 and the fourth elastic panel 4 on the lateral side pulling against each other.

Further, since the fifth elastic panel 5 passes over the back of the motion axis of the wearer's ankle, tension is applied to the fifth elastic panel during dorsiflexion of the foot (when rising on tiptoe or during the push off phase of walking). Thus, the fifth elastic panel 5 raises the lateral heel when the wearer rises on tiptoe. Accordingly, inversion sprain in which the wearer's sole is directed medially can be prevented.

On the contrary, tension is usually applied to the third elastic panel 3 in plantar flexion (when the toes are lowered). Accordingly, it is possible to prevent inversion sprain in which the wearer's sole is directed medially by raising the lateral toes.

EXAMPLE

Figure 3A:
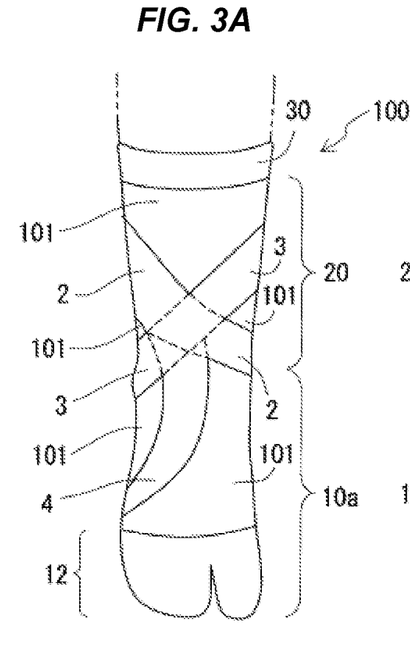
FIG. 3(a) is a front view illustrating the ankle supporter according to the first embodiment as it would be worn on the right foot.
Figure 3B:
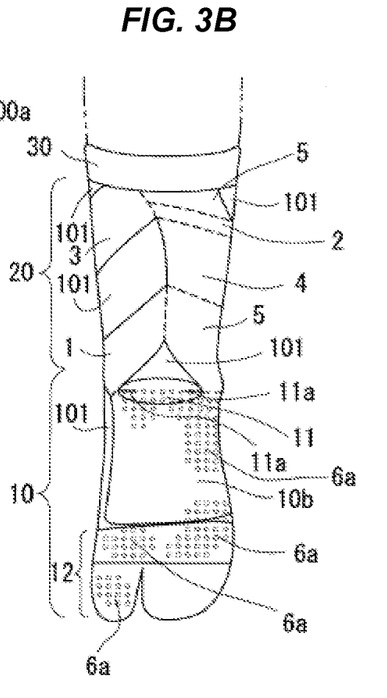
FIG. 3(b) is a rear view illustrating the ankle supporter shown in FIG. 3(a)
Figure 3C:
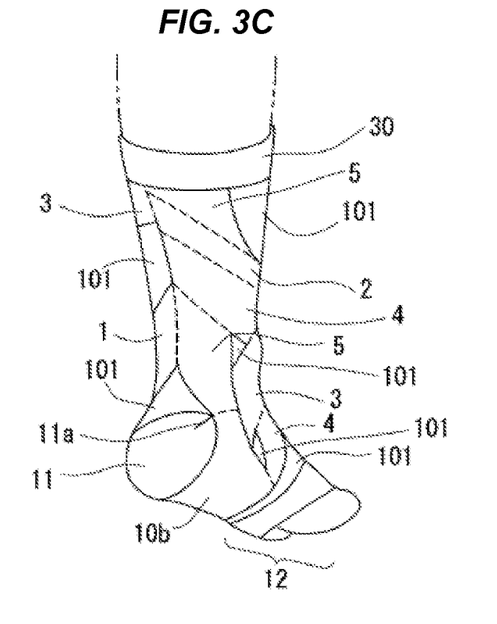
FIG. 3(c) shows the right lateral rear view of the ankle supporter shown in FIG. 3(a).
Figure 4A:
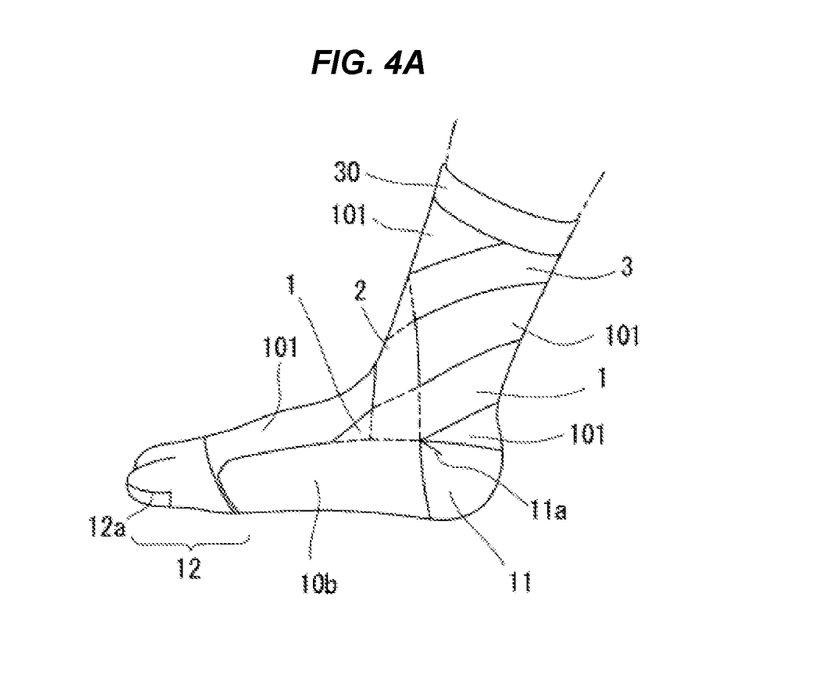
FIG. 4(a) presents the medial view of the ankle supporter shown in FIG. 3(a) and FIG. 4(b) is a lateral view of the ankle supporter shown in FIG. 3(a).
Figure 4B:
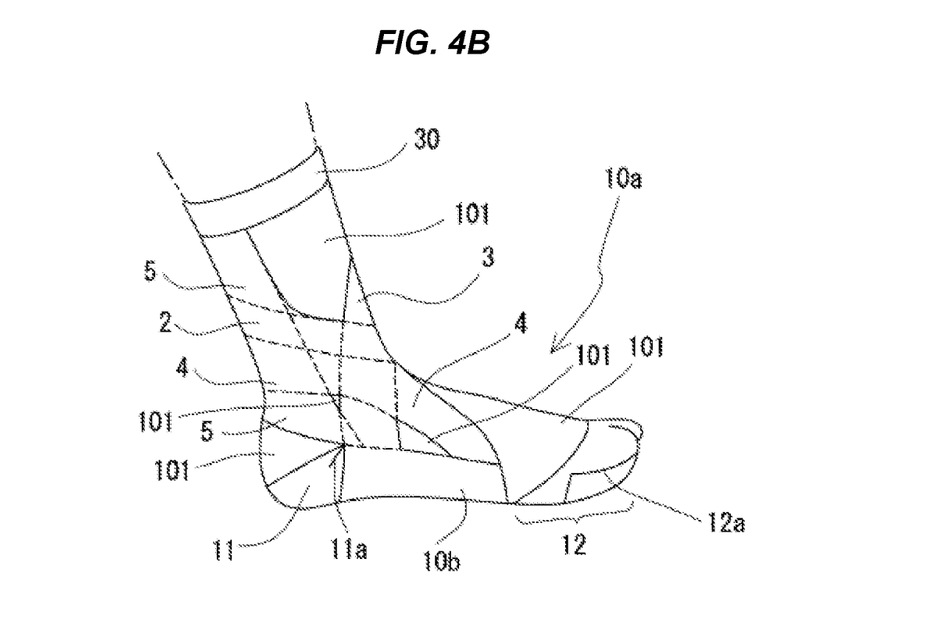
Figure 5A:
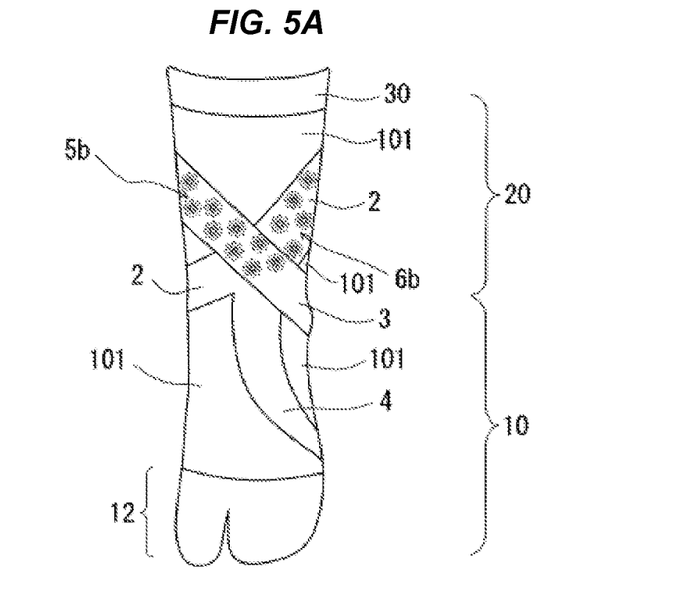
FIG. 5(a) is a rear view illustrating the back fabric of the ankle supporter shown in FIG. 3(a) and FIG. 5(b) is a rear view illustrating the back fabric of the ankle supporter shown in FIG. 3(b).
Figure 5B:
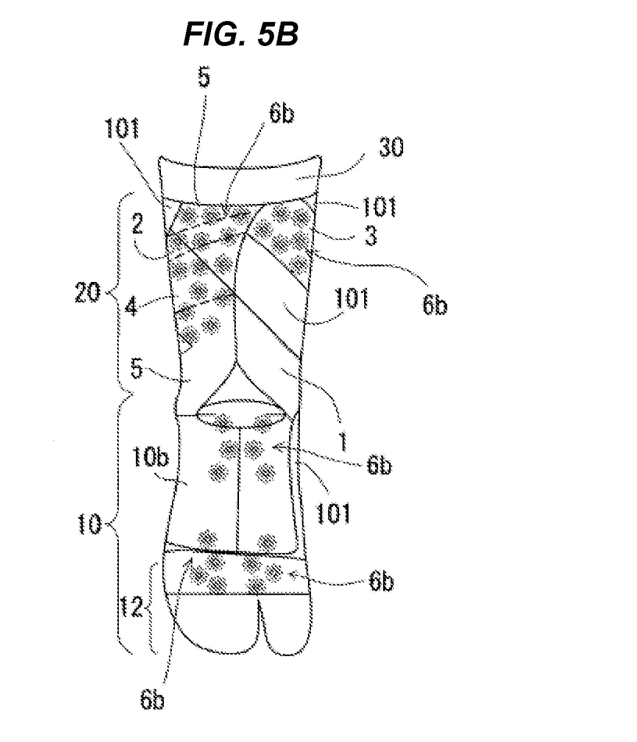

Next, we present an application of the theory described above to a subject wearing socks 100*a* produced by circular knitting according to the design of ankle supporter 100. FIGS. 3 to 5 are shown as references.

In the description below, the right sock 100*a* will be described with reference to FIGS. 3 to 5. Since the left sock 100*a* differs from the right sock only in that the knitted fabric positions of the first elastic panel 1, the second elastic panel 2, the third elastic panel 3, the fourth elastic panel 4, and the fifth elastic panel 5 are bilaterally symmetrical to those of the right sock 100*a*, the left socks will not be shown in the drawings.

According to the embodiment shown in FIGS. 3 and 4, sock 100*a* is produced on a sock knitting machine using knitting yarns including a front yarn, a rear yarn, and a rubber yarn. The sock-knitting machine used in this example was "Lambda Infini" (number of stitches: 144), manufactured by Murata Manufacturing Co., Ltd. Here, a cylindrical knitted fabric was produced by circular knitting. The part corresponding to the toe of the wearer is sewn to form a sock shape.

The sock 100 a is generally divided into three sections: the foot section 10, the body section 20, and a rubber opening section 30 (also referred to herein as rubber section 30) at the top. These sections are knitted with various differences in the base fabric 101.

According to the embodiment, the base fabric 101 is produced using a plain stockinette stitch in which the knitted stitches are continuously arranged in a series and the front and back of the fabric are easily distinguishable from each other.

The foot section 10 includes a heel part 11 (also referred to herein as heel 11) which is formed in the cylindrical knitted fabric so that it corresponds to the heel of the wearer, a toe part 12 (also referred to herein as toe 12) which is formed in the cylindrical knitted fabric so that it corresponds to the toes of the wearer, a foot top part 10*a* (also referred to herein as foot top 10*a*) which is the area above a line connecting the front end of a formation line (gore line) 11*a* of the heel part 11 and the front end of a formation line 12*a* of the toe part 12, and a sole part 10*b* (also referred to herein as sole 10*b*) which is the area below the line connecting the front end of the formation line 11*a* of the heel part 11 and the front end of the formation line 12*a* of the toe part 12.

Further according to the embodiment, the toe 12 may be divided into two parts so that the first toe (big toe) and the other four toes are separately encased. Accordingly, torsion of the socks 100*a* can be prevented when the wearer is walking.

Further according to the embodiment, the toe 12 may be divided into two or more parts. For example, a toe other than the first toe may be divided from the other four toes or several of the toes may be divided from the other toes.

In addition according to the embodiment, to create the heel 11 and toe 12, another knitting yarn (a pile yarn) is fed into the machine in addition to the plain-stitched knitting yarn and the two yarns are both knitted simultaneously so that the plain knitting yarn appears on the front surface and the pile yarn appears on the back surface. Hence, the knitted fabric (hereinafter, referred to as a plain-stitched/pile-stitched fabric) is formed by a pile stitch obtained by enlarging the sinker loop of the pile yarn and extracting the pile in an annular shape. Here, the annular pile serves as an anchor that suppresses positional deviation of the first elastic panel 1, the second elastic panel 2, the third elastic panel 3, the fourth elastic panel 4, and the fifth elastic panel 5 in a manner to be described later.

In this way, the heel 11 and the toe 12 are formed so that the loop-shaped knitted stitch similar to that of a towel is provided on the inside surface of the cloth (the surface that is in contact with the wearer's body surface). Thus, an air layer is formed at the heel 11 and toe 12, providing an improved cushioning property in these areas. Further, when the socks 100*a* are worn with shoes, the loop-shaped knitted stitch provides a cushioning packing that reduces stress from the shoes and absorbs sweat from the wearer due to the excellent water absorbency of this fabric.

Further according to the embodiment, the sole 10*b* is formed in the knitted fabric (hereinafter, referred to as a tuck-stitched/plating-stitched fabric), by a combination of plating-stitching and tuck-stitching. The knitted fabric thus obtained has knitted stitches that are formed together without the need to make a temporary knitted stitch when the cloth is knitted.

Further, in the tuck-stitched/plating-stitched fabric, an additional knitting yarn (for example, a wooly nylon yarn) is fed into the machine along with the tuck-stitched knitting yarn. Accordingly, the longitudinal stretchability of the sole 10*b* of the socks 100*a* is appropriately suppressed. The additional knitting yarn is cut at the boundary between the sole 10*b* and the base fabric 101 (cut boss).

In this way, since the stretch resistance of the sole 10*b* is greater than that of the base fabric 101, lateral slip of the socks 100*a* is prevented. Furthermore, the sole supports the arch of the wearer's foot while serving as an anchor for the elastic panels (the first elastic panel 1, the second elastic panel 2, the third elastic panel 3, the fourth elastic panel 4, and the fifth elastic panel 5) extending from the wearer's sole to the lower leg. Further, this construction has the effect of absorbing and reducing the impact of the foot striking the ground surface.

Further, the socks 100*a* include the first elastic panel 1 which is knitted in a belt-like shape on the medial side of the wearer's foot from the sole 10*b* to the area corresponding to the wearer's Achilles tendon and has a stretch resistance greater than that of the base fabric 101. The second elastic panel 2 is also knitted in a belt-like shape on the medial side of the wearer's foot. The second elastic panel 2 extends from the heel 11 crossing over the foot 10*a* so as to intersect the first elastic panel 1 below an area corresponding to the center of the medial ankle of the wearer. This panel also has a stretch resistance greater than that of the base fabric 101.

In addition according to the embodiment, the first elastic panel 1 and the second elastic panel 2 are knitted using the tuck-stitched/plating-stitched technique similar to that used to construct the sole 10*b*.

In addition, the first elastic panel 1 and the second elastic panel 2 should ideally be formed such that the first elastic panel 1 extends from the wearer's sole to their Achilles tendon and the second elastic panel 2 extends from the heel to the bend of the wearer's ankle so that these panels intersect at a position below the center of the medial ankle part 204 as shown in FIG. 1(*a*). However, in order to integrate the second elastic panel 2 in the circular knitted fabric of the socks, it is necessary to construct a highly stretchable knitted fabric in the flexible heel 11 on the extension line of the second elastic panel 2. This technique is difficult. Therefore according to the embodiment, the second elastic panel 2 is knitted in a belt-like shape from the sole 10b adjacent to the heel 11 crossing over the base of the foot 10a and continuing on the lower leg as shown in FIG. 4(*a*). Further according to the embodiment, the socks 100a may have a configuration in which the heel 11 is not knitted. Instead an opening penetrating the base fabric (a hole anchor) is provided so as to expose the wearer's heel. The second elastic panel 2 is then connected to the hole anchor.

In addition, according to the embodiment shown in FIG. 4(*b*), the socks 100a have a second elastic panel 2 that extends from the lateral side of the wearer's foot to the back of the wearer's foot and is connected through the fifth elastic panel 5 to the rubber section 30 at the cuff of the sock encircling the lower leg. Further, as shown in FIG. 3(*b*), the first elastic panel 1 is connected to the fifth elastic panel 5 on the lateral side of the wearer's foot so that the second elastic panel 2 forms a spiral. Thus, the rubber section 30 serves as an anchor that maintains the positions the first elastic panel 1 and the second elastic panel 2.

However, when the socks 100a are made with a short body 20, the first elastic panel 1 and the second elastic panel 2 may be connected to the rubber section 30 at the medial side of the wearer's foot without the second elastic panel 2 forming a spiral.

Further, the socks 100a include the third elastic panel 3 which is knitted in a belt-like shape on the lateral side of the wearer's foot extending from the heel 11 at the border between the sole 10b and the foot top 10a so as to overlap the area corresponding to the wearer's ankle. This third elastic panel 3 has a stretch resistance greater than that of the base fabric 101. The fourth elastic panel 4 is knitted in a belt-like shape on the lateral side of the wearer's foot extending from the area of the sole 10b near the wearer's fifth toe to the base of the foot top 10a so as to be connected to the third elastic panel 3 near the base of the foot top 10a and extending to the back of the wearer's foot. This fourth elastic panel 4 also has a stretch resistance greater than that of the base fabric 101. The fifth elastic panel 5 is disposed on the lateral side of the wearer's foot extending from the wearer's heel to the rubber 30 at the back of the wearer's foot. This fifth elastic panel 5 also has a stretch resistance greater than that of the base fabric 101.

In addition according to the embodiment, the third elastic panel 3, the fourth elastic panel 4, and the fifth elastic panel 5 are comprised of a tuck-stitched/plating-stitched fabric similar to that used to construct the sole 10b, the first elastic panel 1, and the second elastic panel 2.

In addition, the third elastic panel 3 and the fourth elastic panel 4 should ideally be formed such that the third elastic panel 3 extends from the wearer's heel to the bend at the wearer's ankle and the fourth elastic panel 4 extends from the wearer's sole to the bend at the wearer's ankle so as to overlap the wearer's lateral ankle 205 as shown in FIG. 1(*d*). However, in order to integrate the third elastic panel 3 into the circular knitted fabric of the socks, it is necessary to create a highly stretchable knitted fabric in the flexible heel 11 at the extension line of the third elastic panel 3. This technique is difficult. Therefore according to the embodiment, the third elastic panel 3 is knitted in a belt-like shape from the sole 10b adjacent to the heel 11 extending to the foot top 10a as shown in FIG. 4(*b*). Further according to the embodiment, the socks 100a may have a configuration in which the heel 11 is not knitted. Instead a hole penetrating the base fabric (a hole anchor) is provided so as to expose the wearer's heel. The third elastic panel 3 is then connected to the hole anchor.

In addition according to the embodiment as shown in FIG. 4(*a*), the socks 100a have a third elastic panel 3 that is connected to the rubber section 30 on the medial side of the wearer's foot so that the third elastic panel 3 forms a spiral. Thus, the rubber section 30 serves as an anchor that stabilizes the position of the third elastic panel 3.

However, when the socks 100a have a short body 20, the third elastic panel 3 may be connected to the rubber section 30 on the lateral side of the wearer's foot without the third elastic belt 3 forming a spiral.

Further, on the sole of the heel 11 and toe 12 and on the sole 10b, a slip preventing tread 6 is disposed on the front of the fabric (the surface that is in contact with the shoe) and on the back of the fabric (the surface that is in contact with the wearer's skin).

As shown in FIG. 3(*b*), the slip preventing tread 6 (hereinafter, referred to as the first slip preventing tread 6a) on the front of the fabric is substantially disposed in the half area near the toes and on the heel 11, that is an area excluding the toe bag of the second toe, the third toe, the fourth toe, and the fifth toe in the toe section 12, and an area near the boundary between the heel 11 and the toe 12 on the sole 10b. These treads prevent a positional deviation between the socks 100a and the insole of the shoe.

Further, as shown in FIG. 5(*b*), the slip preventing tread 6 (hereinafter, referred to as the second slip preventing tread 6b) on the back of the fabric is substantially disposed in the half area near the toes and the heel 11, that is an area excluding the toe bag in the toe section 12, and an area near the boundary between the toe 12 and the heel 11 on the sole 10b. These treads prevent a positional deviation between the socks 100a and the sole of the wearer's foot.

Further, as shown in FIG. 5, since the second slip preventing treads 6b are disposed in an area above the foot top 10a on the second elastic panel 2, the third elastic panel 3, and the fifth elastic panel 5 and contacts the wearer's skin, the second slip preventing tread functions as an anchor for the second elastic panel 2 and the third elastic panel 3 and also gives a massage effect to the underlying muscles in that area, contributing to recovery of ankle flexibility.

The first slip preventing tread 6a and the second slip preventing tread 6b are formed by an adhesive resin processing method such as dot processing (powder-dot processing, pace-dot processing, and double-dot processing), powder processing, web processing, and film processing using natural resin or a soft synthetic resin such as polyvinyl chloride, acryl, polyurethane, and silicone as the adhesive resin. Here, the shape of the slip preventing tread is not particularly limited.

In addition according to the embodiment, the first slip preventing tread 6a is formed by the clustering of numerous silicone rubber protrusions (for example, dots). For example, a liquid silicone rubber is applied to a predetermined area of the front of the fabric of the sole 10b using a silk screen printing method and the coated silicon rubber is dried so as to be fixed to the front of the fabric of the sole 10b.

According to the embodiment, the second slip preventing tread 6b is similarly formed by the clustering of numerous silicone rubber protrusions. For example, a liquid silicone rubber is applied to a predetermined area of the back of the fabric of the sole 10b using a silk screen printing method and the coated silicon rubber is dried so as to be fixed to the back of the fabric of the sole 10b.

In addition, the slip preventing tread 6 may be disposed only on the front of the fabric or the back of the fabric. However, when the slip preventing tread is disposed on both the front and the back of the fabric, the socks 100*a*, the wearer's foot, and the insole of the wearer's shoe are integrated without positional deviation. Accordingly, the wearer can walk more stably. Therefore, it is desirable to dispose the slip preventing treads on both surfaces.

In the embodiment, front and rear knitting yarns are used for the plain-stitching/tuck-stitching. Here, the front yarn is composed of 50% cotton and 50% ester and has a single-twist thickness of 30 denier and can be double-knit. The rear yarn is a covered yarn that include a polyurethane core with a thickness of 30 denier and covered by an ester wound yarn having a thickness of 75 denier. However, the invention is not limited to the use of this material. As the front yarn, it is desirable to select a natural fiber such as cotton, wool (cashmere, lamb, or angora), silk, and hemp, a chemical fiber such as acryl, or a material having a sweat-absorbing function, a quick-drying function, or a body temperature-adjusting function in accordance with the demand of the wearer or the cost of the socks 100*a*. Further, as the rear yarn, it is desirable to select nylon, FTY, or an antibacterial or deodorizing material in accordance with the demand of the wearer or the cost of the socks 100*a*.

Further, a wooly nylon yarn with a double-twist thickness of 100 denier is used to form a double-knit tuck-stitched/plating-stitched fabric and double-knit plain-stitched/pile-stitched fabric.

Further, the rubber yarn of the tuck-stitched/plating-stitched fabric is a covered yarn made from a polyether core yarn with a thickness of 260 denier covered by an ester wound yarn with a thickness of 75 denier.

According to the embodiment, the knitted fabrics comprising the first elastic panel 1, the second elastic panel 2, the third elastic panel 3, the fourth elastic panel 4, and the fifth elastic panel 5 of the socks 100*a* are knitted so that the stretch resistance is increased compared to that of the base fabric 101. This is accomplished by changing the number of knitted stitches in the tuck-stitching and reinforcing the knitted fabric by the plating-stitching. However, when the knitted fabrics of the first elastic panel 1, the second elastic panel 2, the third elastic panel 3, the fourth elastic panel 4, and the fifth elastic panel 5 are knitted using a yarn impregnated with resin such as polyester, polyamide, polyurethane, polyethylene (high density and low density), and ethylene vinyl acetate, the stretch resistance can be increased. Thus, the same function and effect can be obtained.

Further, the stretch resistance can also be increased by sewing a tape (an extension preventing tape) such as a narrow cloth to prevent extension or attaching an adhesive tape comprised of an adhesive applied to a strip of material such as cellophane or vinyl to the knitted fabrics of the first elastic panel 1, the second elastic panel 2, the third elastic panel 3, the fourth elastic panel 4, and the fifth elastic panel 5.

Further, the stretch resistance can be also increased by coating liquid resin onto the knitted fabrics of the first elastic panel 1, the second elastic panel 2, the third elastic panel 3, the fourth elastic panel 4, and the fifth elastic panel 5 so that the resin is oxidized and stuck thereto by air, attaching a thin film of resin thereto, or by spraying liquid resin through a sprayer so that the resin is oxidized and stuck thereto by air.

The knitted fabrics comprising the first elastic panel 1, the second elastic panel 2, the third elastic panel 3, the fourth elastic panel 4, and the fifth elastic panel 5 may be fusible interlining fabrics subjected to a resin treatment using an adhesive. In this case, when the adhesive resin such as polyester, polyamide, polyurethane, polyethylene (high density and low density), and ethylene vinyl acetate is heated and pressurized by a flat press machine or a roller press machine after the resin is coated onto the knitted fabric in accordance with a processing method such as dot processing, powder processing, web processing, or film processing, resin can be applied to the knitted fabric.

Figure 6A:
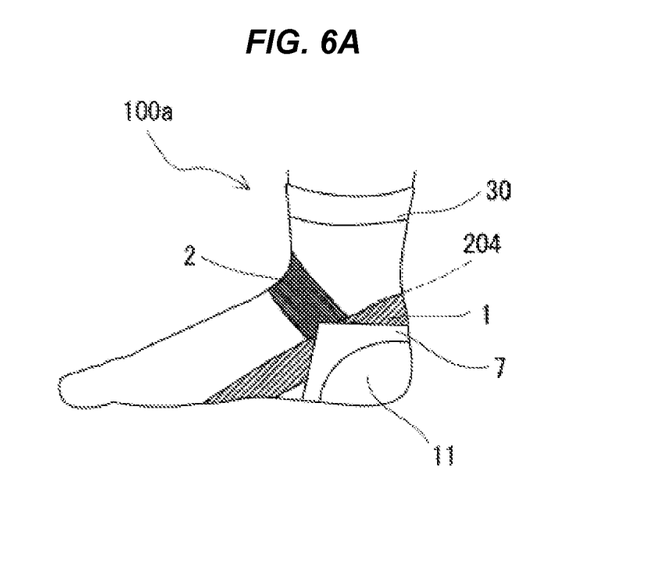
FIG. 6(a) is an explanatory diagram illustrating the resinous sheet used in the first and second elastic panels and FIG. 6(b) is an explanatory diagram illustrating the resinous sheet used in the third and fourth elastic panels.
Figure 6B:
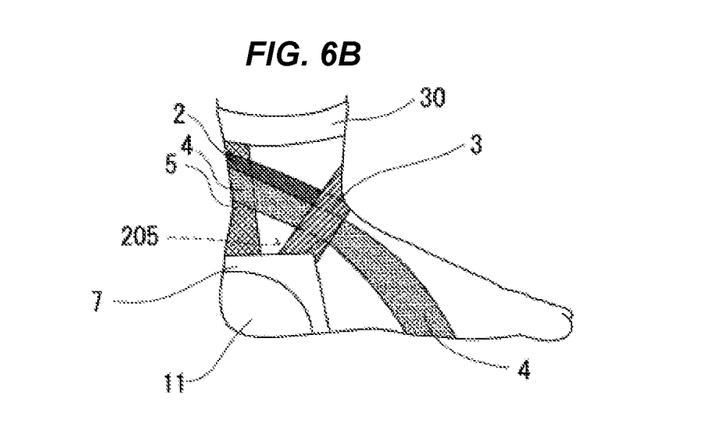

In addition according to the embodiment, the heel 11 is knitted in the plain-stitched/pile-stitched fabric, but the anchor function may not be sufficient due to a positional deviation with respect to the wearer's heel. Since according to the embodiment, the heel 11 is configured such that the annular resinous sheet-shaped body 7 is disposed so as to be thermally press-bonded to the area near the boundary between the sole 10*b* and the body 20 as shown in FIG. 6, friction at the wearer's heel is increased. Hence, positional deviation with respect to the wearer's heel is suppressed and an anchor function is sufficiently exhibited.

Further according to the embodiment, a production method has been described in which the elastic panels (the first elastic panel 1, the second elastic panel 2, the third elastic panel 3, the fourth elastic panel 4, and the fifth elastic panel 5) of the socks 100*a* are constructed in the cylindrical knitted fabric by circular knitting, but the invention is not limited to this production method. For example, a belt-shaped material may be sewn to the sock base or a cloth may be constructed of a plurality of parts sewn together so as to produce the socks 100*a*.

Figure 7A:
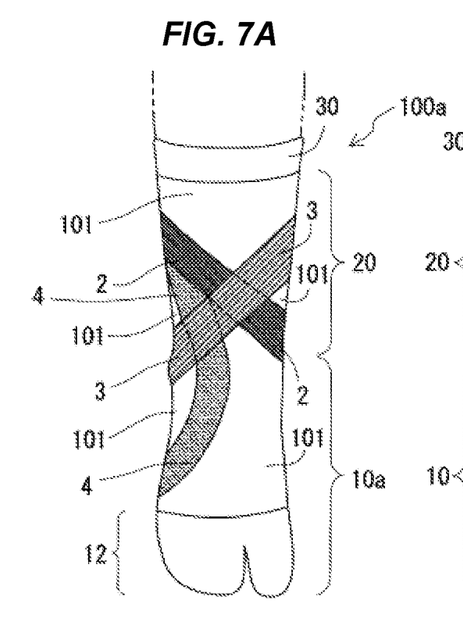
FIG. 7(a) is a front view illustrating a right ankle supporter according to the first embodiment.
Figure 7B:
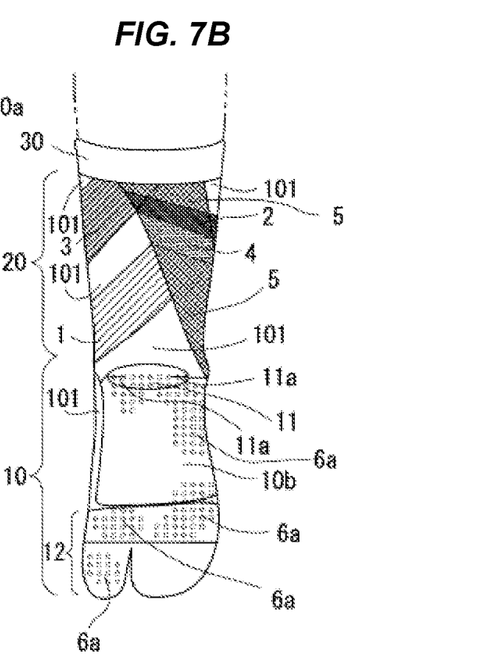
FIG. 7(b) is a rear view of the ankle supporter shown in FIG. 7(a)
Figure 7C:
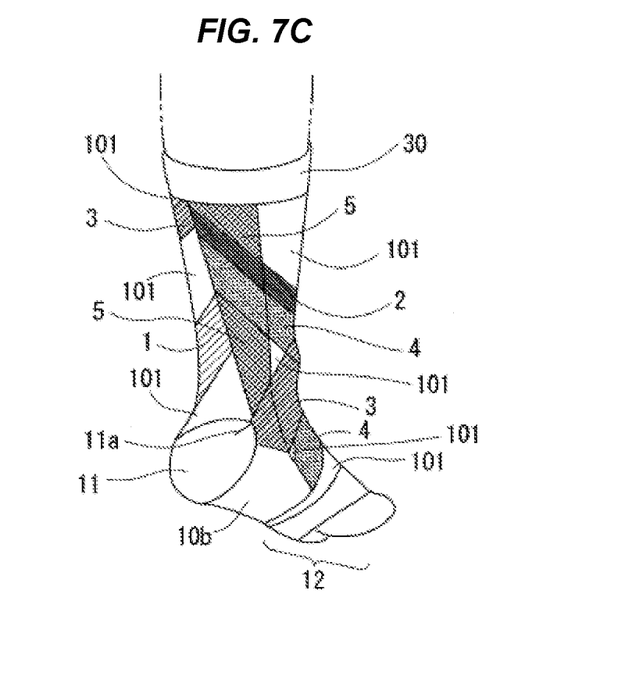
FIG. 7(c) illustrates the lateral rear view of the ankle supporter shown in FIG. 7(a).
Figure 8A:
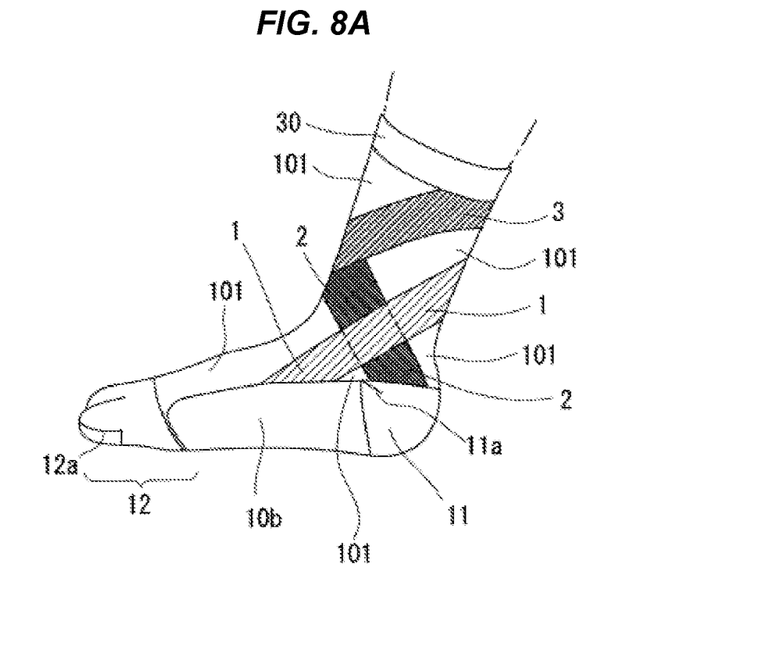
FIG. 8(a) is a medial view of the ankle supporter shown in FIG. 7(a) and FIG.
Figure 8B:
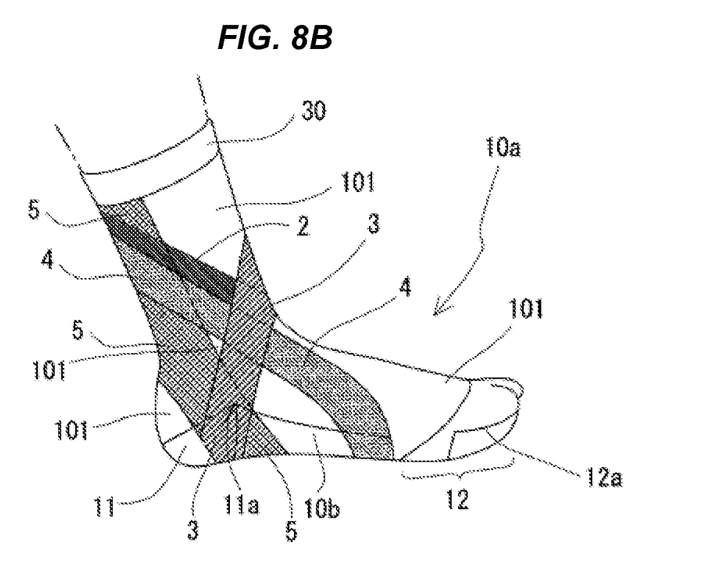

In particular, when a belt-shaped material is sewn to the sock base, the method of sewing the panels including the first elastic panel 1, the second elastic panel 2, the third elastic panel 3, the fourth elastic panel 4, and the fifth elastic panel 5 shown in FIGS. 7 and 8 is considered instead of a method of knitting the first elastic panel 1, the second elastic panel 2, the third elastic panel 3, and the fourth elastic panel 4 shown in FIGS. 3 and 4 in the circular knitted fabric.

EXPLANATIONS OF LETTERS OR NUMERALS

1 FIRST ELASTIC PANEL
2 SECOND ELASTIC PANEL
3 THIRD ELASTIC PANEL
4 FOURTH ELASTIC PANEL
5 FIFTH ELASTIC PANEL
6 SLIP PREVENTING TREAD
6*a* FIRST SLIP PREVENTING TREAD
6*b* SECOND SLIP PREVENTING TREAD
7 SHEET-SHAPED BODY
8 ZIPPER
10 FOOT
10*a* FOOT TOP
10*b* FOOT SOLE
11 HEEL
11*a* FORMATION LINE
12 TOE
12*a* FORMATION LINE
20 BODY
30 RUBBER SECTION
100 ANKLE SUPPORTER
100*a* SOCKS
101 BASE FABRIC
201 TALUS
202 CALCANEUS
203 TIBIA
204 MEDIAL ANKLE
205 LATERAL ANKLE

The invention claimed is:

1. An ankle supporter, comprising:
a base fabric adapted to surround at least an ankle of a wearer;
a first elastic panel which is adapted to be disposed in a belt shape on a first part of the base fabric corresponding to a medial side of the wearer's foot from a sole to an area corresponding to an Achilles tendon of the wearer, and which extends below an area corresponding to a center of a medial ankle part of the wearer, and which has a stretch resistance greater than that of the base fabric;
a second elastic panel which is adapted to be disposed in a belt shape on a second part of the base fabric corresponding to the medial side of the wearer's foot from a heel to a base of a dorsum of the wearer so as to intersect the first elastic panel at the area corresponding to the center of the wearer's medial ankle part while being located below the first elastic panel, and which has a stretch resistance greater than that of the base fabric;
a third elastic panel which is adapted to be disposed in a belt shape on a third part of the base fabric corresponding to a lateral side of the wearer's foot from the heel to the base of the wearer's dorsum so as to overlap a lateral ankle part of the wearer, and which has a stretch resistance greater than that of the base fabric;
a fourth elastic panel which is adapted to be disposed in a belt shape on a fourth part of the base fabric corresponding to the lateral side of the wearer's foot from an area of the sole near a fifth toe of the wearer to the base of the wearer's dorsum so as to be connected to the third elastic panel in the vicinity of the base of the dorsum, and which has a stretch resistance greater than that of the base fabric;
a rubber opening section which is adapted to be disposed on a part of the base fabric corresponding to an area above the first, second, third, and fourth elastic panels and that is adapted to encircle a lower leg of the wearer, and
a fifth elastic panel which is adapted to be disposed in a belt shape on a fifth part of the base fabric corresponding to the lateral side of the wearer's foot from the heel along the back of the foot and connecting to the rubber opening section, and which has a stretch resistance greater than that of the base fabric.

2. The ankle supporter according to claim 1,
wherein the ankle supporter consists of socks, each of which includes a foot section consisting of a toe part, a heel part, a foot top part and a sole part, a body section, and the rubber opening section, with the foot section, the body section, and the rubber opening section being differently knitted in the base fabric,
wherein the first elastic panel is knitted and adapted to extend from the sole part to the area corresponding to the Achilles tendon of the wearer, wherein the second elastic panel is knitted and adapted to extend from the heel part to a part corresponding to the base of the foot top part so as to intersect the first elastic panel below the center of the medial ankle of the wearer,
wherein the third elastic panel is knitted and adapted to extend from the heel part to the part corresponding to the base of the foot top part so as to overlap the part corresponding to the wearer's lateral ankle part,
wherein the fourth elastic panel is knitted and adapted to extend from the area of the sole part near the wearer's fifth toe to the part corresponding to the base of the foot top part so as to be connected to the part corresponding to the third elastic panel near the base of the foot top part, and
wherein the fifth elastic panel is knitted and adapted to extend from the heel part along the back of the foot section so as to be connected to the rubber opening section.

3. The ankle supporter according to claim 2,
wherein a stretch resistance of the sole part is greater than the stretch resistance of the base fabric.

4. The ankle supporter according to claim 2, wherein the heel part, the toe part, and the sole part on a sole side of the base fabric are constructed so that a slip preventing tread is disposed on the front and/or back of the base fabric.

* * * * *